(12) United States Patent
Hudon

(10) Patent No.: US 6,524,281 B1
(45) Date of Patent: Feb. 25, 2003

(54) NEEDLE PROTECTION DEVICE FOR USE WITH A VIAL

(75) Inventor: Lawrence P. Hudon, Hinsdale, NH (US)

(73) Assignee: Portex, Inc., Keene, NH (US)

( * ) Notice: Subject to any disclaimer, the term of this patent is extended or adjusted under 35 U.S.C. 154(b) by 0 days.

(21) Appl. No.: 09/549,337

(22) Filed: Apr. 14, 2000

(51) Int. Cl.[7] .............................. A61M 5/00; A61M 5/32
(52) U.S. Cl. ........................ 604/263; 604/192; 604/198
(58) Field of Search .............................. 604/110, 181, 604/187, 192, 197, 198, 218, 232, 234, 257, 240–243, 263; 128/919

(56) References Cited

U.S. PATENT DOCUMENTS

| | | |
|---|---|---|
| 4,659,330 A | 4/1987 | Nelson et al. |
| 4,795,443 A | 1/1989 | Permenter et al. |
| 4,931,040 A * | 6/1990 | Haber et al. ............... 604/110 |
| 5,154,285 A * | 10/1992 | Hollister ..................... 206/365 |
| 5,312,369 A | 5/1994 | Arcusin et al. |
| 5,350,367 A * | 9/1994 | Stiehl et al. ............... 604/232 |
| 6,036,675 A * | 3/2000 | Thorne et al. .............. 604/232 |

* cited by examiner

*Primary Examiner*—Michael J. Hayes
(74) *Attorney, Agent, or Firm*—Louis Woo

(57) ABSTRACT

A needle protection device for a vial, or capsule, has a housing hingedly or flexibly connected to a needle collar by a hinge. The collar has a main portion configured to fit about at least a portion of the body of the vial and an extension configured to fit about at least a portion of the neck of the vial. A needle hub, movable along the neck of the vial and to which a needle extends, is interposed between the body and neck of the vial. The hub has a skirt portion that could be moved along the neck of the vial for capping or overlapping the extension of the collar to thereby non-removably secure the collar to the vial. An improved syringe assembly is effected when a vial of the instant invention is placed within a vial holder applicator, such as for example a CARPUJECT applicator. Once firmly positioned within the applicator, a mechanism integral to the applicator is actuated to move the skirt portion of the hub and the collar extension that fits about the neck of the vial relatively towards each other so that the collar extension is capped by the hub skirt portion, thereby securely coupling the collar to the vial. A rod movable along the length of the applicator is mated with a plunger movable along the body of the vial to effect the syringe assembly. The housing hingedly connected to the collar is pivotable relative to the vial to envelop the needle extending from the hub, thereby ensuring that the needle, once contaminated, is prevented from being further exposed.

10 Claims, 3 Drawing Sheets

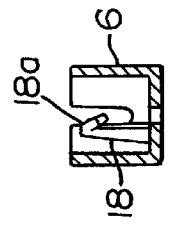
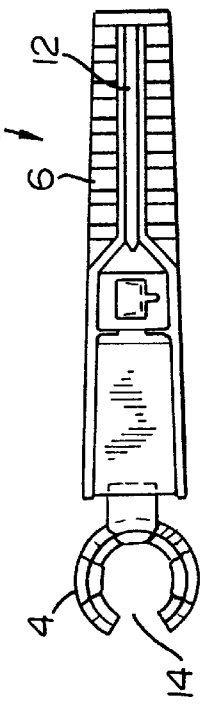
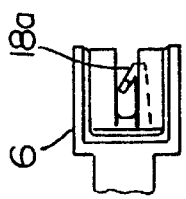
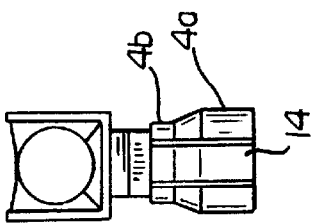
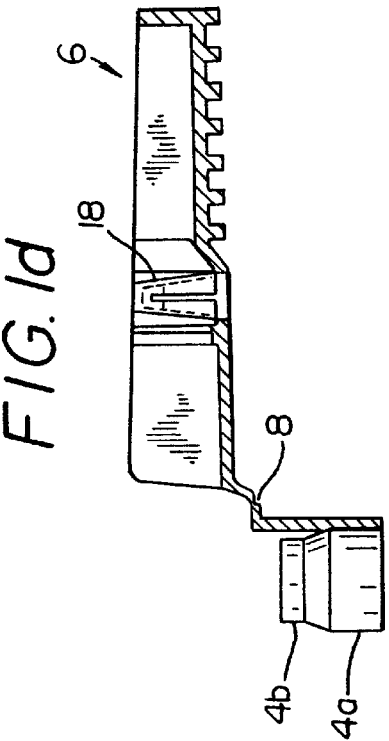
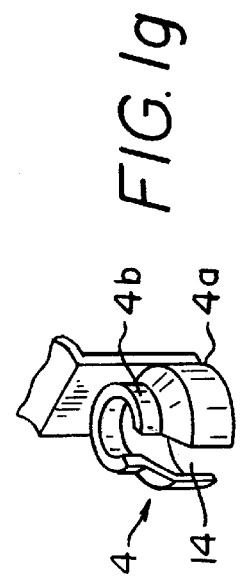
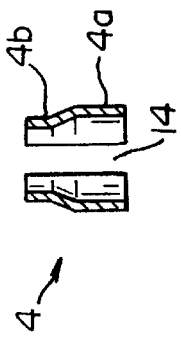

NEEDLE PROTECTION DEVICE FOR USE WITH A VIAL

RELATED APPLICATIONS

This application is related to patent application Ser. No. 09/227,819 now U.S. Pat. No. 6,334,857 filed Jan. 11, 1999 entitled "Needle Protection Apparatus Used With A Vial", assigned to the same assignee as the instant application. The disclosure of the '819 application is incorporated by reference to the instant application.

FIELD OF THE INVENTION

The present invention relates to needle protection devices, and more specifically a needle protection device that could securely couple to a vial having a needle extending therefrom for preventing the needle, once contaminated, from being further exposed to the environment.

BACKGROUND OF THE INVENTION

A needle protection device for use with a vial that contains medicament to be used with applicators such as the TUBEX and CARPUJECT applicators is disclosed in the aforenoted related '819 application. One embodiment of the related device disclosed in the '819 application has a collar that slidably fits over the hub of a vial and secures thereto by means of a number of extending fingers. Another embodiment of the '819 device has an open collar that mounts about the vial. A pair of interlocking extensions from the collar coact to secure the collar about the vial. Although work well, these devices fail to take full advantage of the structure of the vial itself and the interaction between the vial and the applicator in order to securely couple the needle protection device to the vial.

SUMMARY OF THE INVENTION

The present invention needle protection device is to be used with a vial or capsule that has a body and a neck extending therefrom. The vial has a needle hub either interposed between the neck and the body of the vial or fitted over the neck of the vial. A needle extending from the hub is fluidly connected to the vial. The needle hub has a skirt portion that is movable along the neck of the vial.

The needle protection device of the instant invention has a needle protection housing hingedly or flexibly connected to an open ended collar. The collar has a main portion that fits about at least a portion of the body of the vial, and an extension that fits about at least a portion of the neck of the vial.

To couple the collar to the vial, with the needle hub, and the skirt portion thereof, moved as far away from the body of the vial as feasible, the collar of the needle portion housing is snap fitted about the body and the neck of the vial. Once the collar is thus fitted to the vial, the hub fitted over the neck of the vial is moved towards the body of the vial, so that the skirt portion thereof caps or overlaps the extension of the collar fitted about the neck of the vial. When thus capped, the collar, and therefore the needle protection housing, is securely coupled to the vial. Thereafter, to prevent the needle that extends from the vial from being exposed to the environment, the housing only needs to be pivoted, relative to the collar, to the longitudinal axis of the vial, to thereby envelop the needle extending from the vial.

An improved syringe assembly is effected when a vial fitted with the needle protection housing as described above is placed in a vial applicator, such as for example a CARPUJECT applicator. Once firmly seated within the cavity of the vial applicator, a mechanism integral to the applicator is actuated to apply a biasing force against the body of the vial to force the skirt portion of the needle hub and the collar extension to move relatively towards each other, with the end result being that the collar extension is capped by the hub skirt portion, thereby firmly coupling the needle housing to the vial, which in turn is held by the biasing force within the cavity of the holder applicator. To use, a rod movable along the length of the applicator is mated to a plunger seal or gasket that is movable within the body of the vial for effecting a plunger, which, when pushed, will cause the medicament stored in the vial to be ejected out of the needle. Once used, the needle is prevented from being further exposed by being enveloped by the needle housing of the syringe assembly.

It is therefore an objective of the present invention to provide a vial securely fitted with a needle protection housing.

It is yet another objective of the present invention to provide an improved syringe assembly made up of a vial, a needle protection housing securely coupled thereto, and a holder applicator into which the vial is securely held.

It is still another objective of the present invention to provide a needle protection housing that could be retrofitted to existing vials or capsules in which medicament may be stored.

BRIEF DESCRIPTION OF THE FIGURES

The above-mentioned objectives and advantages of the present invention will become apparent and the invention itself will be best understood with reference to the following description of embodiments of the present invention taken in conjunction with the accompanying drawings, wherein:

FIG. 1*a* is a top view of the needle protection device of the present invention, the housing of the device being positioned at right angle relative to the collar of the device to which it is flexibly or hingedly attached;

FIG. 1*b* is an end view illustrating the hook in the housing of FIG. 1*a*;

FIG. 1*c* is a cross-sectional view of the FIG. 1*a* housing;

FIG. 1*d* is a side view of the FIG. 1*a* device;

FIG. 1*e* is a front view of the collar of FIG. 1*a*;

FIG. 1*f* is an end view of the FIG. 1*d* device;

FIG. 1*g* is a perspective view of the collar of the instant invention device showing an opening along the circumference of the collar;

DETAILED DESCRIPTION OF THE PRESENT INVENTION

Figure 2:
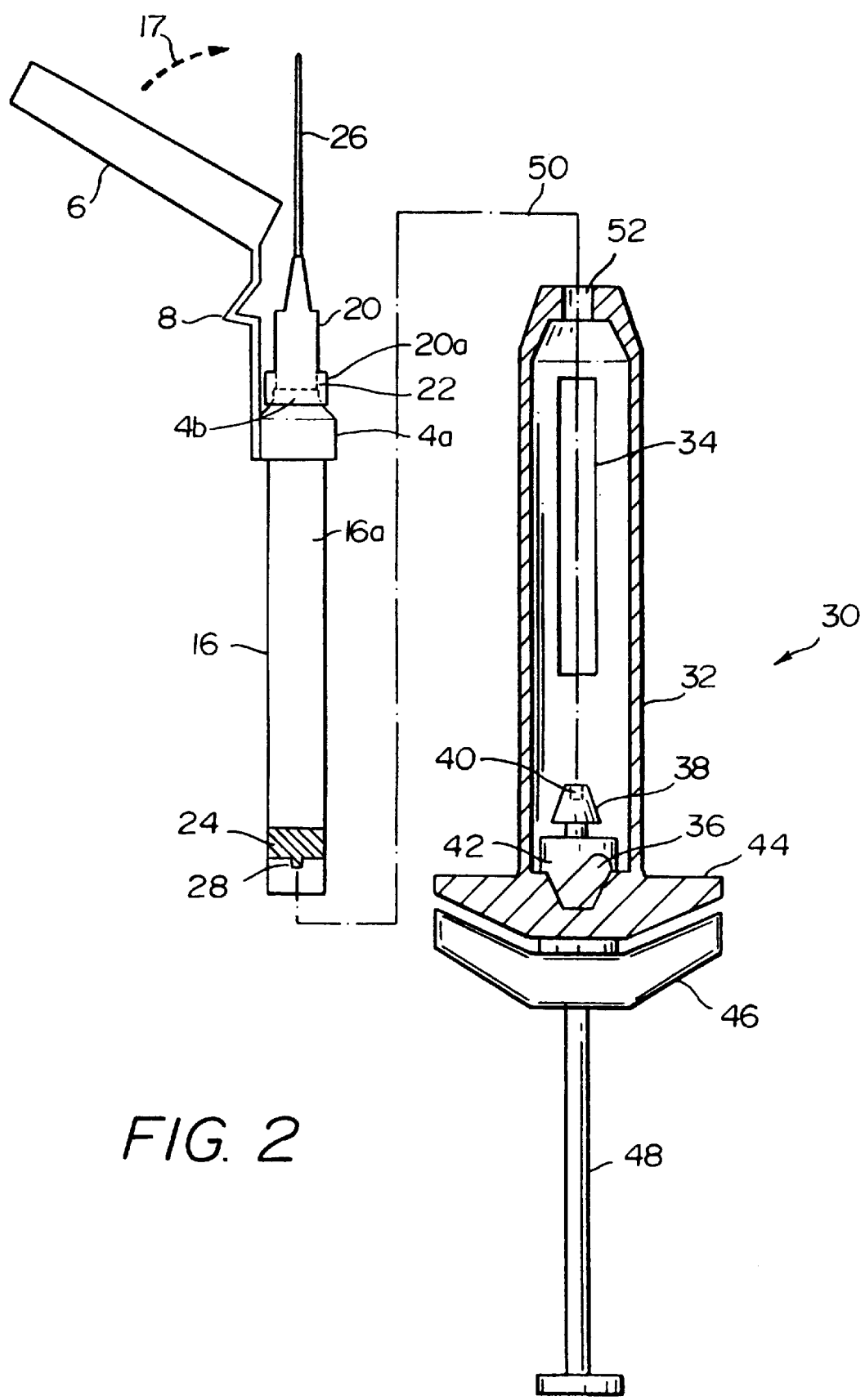
FIG. 2 is an illustration of the inter-relationship among the device of FIG. 1*a*, a vial to which the device is affixed, and a holder applicator for use with the vial.

With reference to FIGS. 1*a*–1*d*, a needle protection device 2 of the instant invention is shown to include a collar 4 and a needle housing 6 movably connected thereto by means of a flexible hinge 8. As best shown in FIGS. 1*e*–1*g*, collar 4 is structured in the form of a non-fully closed ring, an opening 14 along its circumference providing the break to the collar. Collar 4 is further shown to have a main portion 4*a* and an extension 4*b*. The respective dimensions of portion 4*a* and extension 4*b* are configured to form fit about the corresponding body and neck of a vial, such as for example vial 16 shown in FIGS. 2 and 3.

Figure 3:
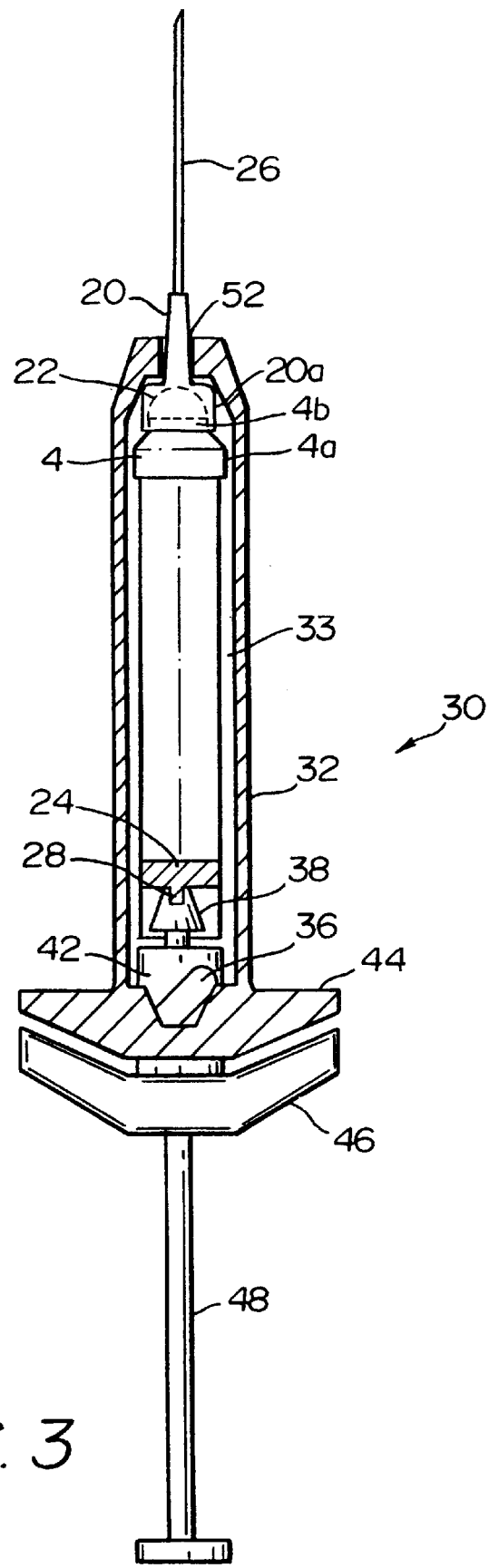
FIG. 3 is an illustration of the improved syringe assembly of the present invention, sans the housing.

Housing 6 of device 2 has formed along the length thereof a longitudinal slot 12 wherethrough a needle, such as for example needle 26 shown in FIGS. 2 and 3, passes. As shown in FIG. 2, needle 26 is enveloped by housing 6 when the latter is pivoted in the direction designated by arrow 17 to a position along the longitudinal axis of vial 16, or needle 26.

To prevent relative movement between needle 26 and housing 6, a locking means is provided to housing 6 to fixedly retain needle 26 within housing 6 once needle 26 is enveloped by housing 6. Such locking means could be for example a latch or a hook 18 integrated to the inside of housing 6 that fixedly grasps needle 26 once finger 18a of hook 18 snaps over needle 26, as housing 6 is pivoted into alignment along the longitudinal axis of vial 16.

With reference to FIGS. 2 and 3, vial 16 about which needle protection device 2 is fitted is shown to include a main body 16a, a neck 22 extending from body 16a, and a needle 26 extending from and in fluid communication with neck 22. As is well known, a needle 26 covers the proximal end of needle 26. Hub 20 has a base 20a that covers and seals neck 22 of vial 16. In practice, needle 26 is molded to and extends from hub 20 so as to be in fluid communication with the medicament stored in vial 16. Vial 16 is sealed at its other end by an elastomeric gasket 24 that is movable along its interior circumferential wall 16a. A screw 28 is molded to gasket 24 to provide connection thereto.

Figure 4:
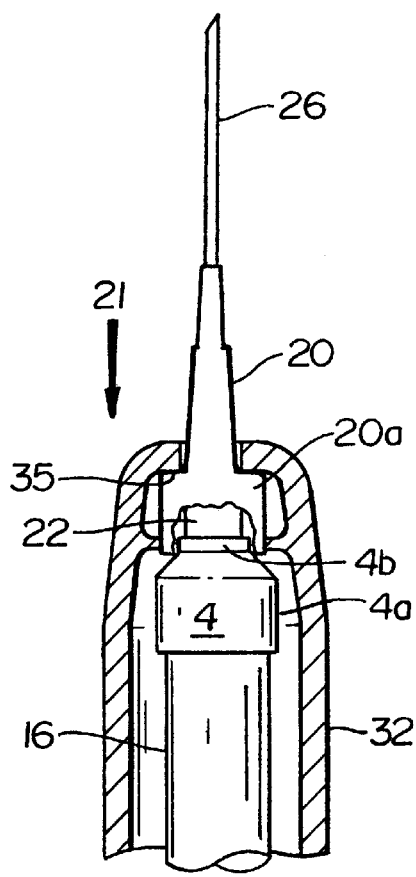
FIG. 4 is a semi-exposed partial view illustrating the interrelationship between the vial, the collar sans its housing that fits about the vial, the needle hub that fits over the neck of the vial, and the holder applicator whereinto the vial is placed.

As best shown in FIGS. 2, 3, and 4, base 20a extends from needle hub 20. Note that base 20a has a large cross-sectional area than that of the main body of hub 20. As a consequence, a void exists between neck 22 of vial 16 and base 20a of hub 20. In other words, base 20a forms a skirt that overlaps neck 22 of vial 16. This space provided by base 20a is of a dimension sufficient to fit over extension 4b of collar 4, as best shown in the semi-exposed partial view of FIG. 4. For the sake of simplicity in the understanding of the invention, housing 6, which in actuality is flexibly connected to collar 4, is not shown in FIG. 4.

During the manufacturing process of a vial such as for example vial 16 as shown in the figures, the inventor has found that hub 20 is not fixedly mounted to neck 22 of vial 16. Rather, hub 20 is non-fixedly coupled to neck 22 such that it is movable longitudinally relative to neck 22 of vial 16. Seizing onto this relationship between the needle hub and the vial, the inventor has designed collar 4 into the particular shape and structure as described herein so as to take full advantage of the relationship between hub 20 and neck 22 of the vial 16. That is, as was mentioned previously, collar 4 is designed to have a main portion 4a that form fits about a portion of the main body of vial 16 and an extension 4b that form fits about at least a portion of neck 22 that extends from the main body of vial 16.

To secure device to vial 16, collar 4 is snap fitted about vial 16. This is possible because collar 4 is made of a plastic material that has a given amount of flexibility so that collar 4 on either side of opening 16 would flex to accept and then embrace vial 16, as collar 4 first flexes and then returns to its original state. At the same time, extension 4b of collar 4 likewise form fits about at least a portion of neck 22. Once collar 4 is fitted about vial 16, hub 20 may be moved in the direction towards the main body of vial 16 so that its base skirt portion 20a caps over extension 4b of collar 4 per directional arrow 21 as shown in FIG. 4. As a consequence, collar 4, and therefore device 2, is securely coupled to vial 16.

Also shown in FIGS. 2 and 3 is a holder applicator 30, represented for example by a conventional CARPUJECT applicator, wherein vial 16 could be fitted. Holder 30 includes an elongated housing 32 having a cavity 33. One side of housing 32 is opened to the environment and an aperture 34 is formed at its opposing side. Housing 32 further has an opening 52 at one of its ends and a finger grip base 44 formed its other end. A bore extends through base 44.

Inserted through the bore of base 44 is a cylinder 42 that extends from a base 46 of substantially similar shape to grip 44. Cylinder 42 has a groove 36 that mates with a bump protrusion (not shown) formed at a surface of the bore of base 44 for guiding cylinder 42 when it is turned in sync with the rotation of base 46. When cylinder 42 is turned to either of its two extreme end positions, absent an external force, it is locked into position by the bump protrusion.

A bore, not shown, extends along the length of cylinder 42. A rod 48, freely coupled to base 46 through the bore of cylinder 42, is movable along the length of holder 30. Rod 48 has a head 38 with a threaded portion 40 formed therein for mating with screw 28 extending from sealing gasket 24 of vial 16.

Base 46, together with cylinder 42 extending therefrom, forms an actuable mechanism for securely maintaining vial 16 within holder 30 and for non-removably securing protection device 2 to vial 16. Both objectives are achieved as follows.

Housing 32 is prepared to accept vial 16. To do that, base 46 is turned counterclockwise (or clockwise) to its lowermost position so as to lower a substantial portion of cylinder 42 into the bore of finger grip base 44. Vial 16 is then placed into cavity 33 of housing 32, with opening 52 providing access for needle 26, and hub 20, extending from vial 16 to extend beyond holder 30. Thereafter, base 46 is turned in a counter direction to raise cylinder 42 towards vial 16. With base 46 turned to its extreme position, the top of cylinder 42 not only comes into contact with the lowermost end of vial 16, but it also forces the uppermost portion of vial 16 into contact with shoulder 35 of housing 32. See FIG. 4. As a consequence, a biasing force is applied against vial 16 and particularly against neck 22 thereof by the underside of shoulder 35.

In view of the fact that neck 22 of vial 16 is covered by hub 20, the biasing force against vial 16 in fact is applied against hub 20, thereby forcing hub 20 to move towards the main body of vial 16. As a result, skirt portion 20a of hub 20 overlaps extension 4b of collar 4. Putting it differently, extension 4b of collar 4 is capped by skirt portion 20a of hub 20 so that collar 4 is securely coupled to vial 16, and vial 16 in turn is securely held within cavity 33 of holder 30.

Line 50 of FIG. 2 illustrates how vial 16, with needle protection device 2 already fitted thereto, is fitted within cavity 32 of holder 30 to effect the needle protection syringe assembly of FIG. 3.

The syringe assembly of FIG. 3 operates as follows. With vial 16 properly fitted to holder 30, and hub 20 being biased against neck 22 of vial 16, rod 48 of holder 30 is mated to plunger 24 of vial 16 by threading portion 38 of rod 48 to screw 28 of gasket 24. The combination of rod 48 and plunger 24 thus effects a plunger means for enabling the medicament stored in body 16a of vial 16 to be ejected through needle 26. This is done by rod 48 pushing gasket 24 towards neck 22 of vial 16 for ejecting the medicament out of needle 26.

Note that a vial absent the hub structure as described above may also be used to effect the syringe assembly of the instant invention. It is envisioned that a collar such as collar 4 discussed above is molded to form fit the neck of such hubless vial, i.e., body 4a fitting about the body 16 while extension 4b form fitting about a portion of neck 22 of vial 16. The collar is then acted upon by the same biasing force as discussed above, so that collar 4 is sandwiched between shoulder 35 of housing 32 and neck 22 of vial 16 so as to be securely held in place thereby. For this embodiment, shoulder 35 of housing 32 may be configured to have a slight concave portion for capping extension 4b of collar 4. Without saying, a housing protection housing such as 6 is pivotally connected to collar 4.

Once vial 16 is properly fitted to holder 30 and collar 4 securely coupled and held in place, to operate, a patient is pricked with needle 26. Rod 48 of holder 30 is then pushed, thereby causing gasket 24 to move along vial 16 to forceably eject the medicament stored in vial 16 through needle 26 into the patient. Afterwards, needle 26 is withdrawn from the patient and housing 6 is pivoted to align along the longitudinal axis of vial 16 to envelop needle 26. As needle 26 is being enveloped by housing 6, finger 18a of hook 18 snaps over needle 26 to thereby fixedly retain needle 26 within housing 6. Portion 40 of rod 48 could then be unthreaded from screw 28 of gasket 24, and base 46 turned to lower cylinder 42 away from vial 16, to thereby release its biasing force on vial 16. Vial 16 could then be removed from holder 30 and discarded.

It should be appreciated that the present invention is subject to many variations, modifications, and changes in detail. For example, even though the syringe assembly of the instant invention has been described as being used to inject a patient with medicament stored in the vial, it could very well be that the vial is empty when it is fitted to the applicator, so that instead of being used for ejection, the syringe assembly of the instant invention could be used for withdrawing body fluid from a patient. Irrespective of how the syringe assembly of the instant invention is to be used, the fact remains that each vial of the assembly is securely fitted with a collar that has pivotally attached thereto a needle protection housing for enveloping a contaminated needle. Thus, all matter described throughout this specification and shown in the accompanying drawings should be interpreted as illustrative only and not in a limiting sense. Accordingly, it is intended that this invention be limited only by the spirit and scope of the hereto appended claims.

What is claimed is:

1. In combination, a vial having a neck, a hub mounted about said neck, a needle extending from said hub, a collar fifted about said vial, said collar having an extension that fits about the neck of said vial, a holder for accepting said vial, a mechanism working cooperatively with said holder for maintaining said vial in said holder, said mechanism actuable to apply a biasing force against said hub, said hub having a skirt portion that, when biased by said force, is driven to overlap said extension of said collar to thereby fixedly couple said collar to said vial.

2. Combination of claim 1, further comprising:
a housing movably coupled to said collar, said housing pivotable to a position in alignment along the longitudinal axis of said vial to envelop said needle.

3. Combination of claim 1, further comprising:
locking means integrated to said housing for preventing said needle and said housing from moving away relative to each other once said housing is pivoted to envelop said needle.

4. Combination of claim 1, wherein said holder comprises an elongated member having a cavity whereinto said vial is placed, said holder further having respective openings at both of its ends, one of said openings for providing access for said needle to extend beyond said holder, the other of said openings providing a path for a rod to extend from outside of said holder to within the interior of said vial to mate with a plunger movably fitted within said vial;
wherein when said rod is pushed towards the neck of said vial, said plunger forces any medicament stored in said vial to be ejected through said needle.

5. Combination of claim 1, wherein said mechanism comprises a turnable base that, when rotated to one direction, would come into contact with the end of the body of said vial away from said neck for applying a force against said vial to thereby indirectly apply said biasing force against said hub.

6. Apparatus, comprising:
a vial having a body, a neck extending from said body and a needle extending from said neck;
a housing for enveloping said needle, said housing having a collar that is configured to fit to said vial, said collar having a portion that is adapted to clamp about said body of said vial and an extension that is adapted to fit about at least a portion of the neck of said vial;
wherein said vial has a needle hub having a skirt portion covering and movable along said neck, and
wherein said extension of said collar is fitted to said neck of said vial so that said skirt portion overlaps said extension of said collar for fixedly coupling said collar to said vial once said collar and said extension are fitted to said vial and its neck, respectively, and said skirt portion of said hub is moved to overlap said extension.

7. A method of attaching a needle protection housing to a vial having a body, a neck extending from said body and a needle extending from said neck, a hub having a skirt portion that is movable along said neck of said vial, comprising the steps of:
a) integrating a collar to said housing, said collar having a portion that clamps about the body of said vial and an extension that fits about at least a portion of said neck of said vial;
b) securing said housing to said vial by means of said collar; and
c) moving said hub to position said skirt portion to overlap said extension of said collar.

8. Method of claim 7, wherein said step a further comprises the step of:
attaching said housing to said collar via a hinge, said housing pivotable about said hinge to a position along the longitudinal axis of said vial to envelop said needle.

9. Method of claim 7, wherein said step b further comprises the step of:
fitting said collar to said vial via an opening at a location along the circumference of said collar.

10. Method of claim 7, further comprising the steps of:
placing said vial secured with said collar into a holder, said holder having one end for biasing against the neck of said vial and a mechanism for applying a biasing force against the other end of the body of said vial away from said neck; and
actuating said mechanism to apply a force against said other end of the body of said vial to push said vial towards said one end of said holder to thereby move said skirt portion and said extension relatively towards each other until said skirt portion overlaps said extension of said collar for fixedly coupling said collar to said vial.

* * * * *